United States Patent
Han et al.

(10) Patent No.: US 6,378,357 B1
(45) Date of Patent: Apr. 30, 2002

(54) METHOD OF FLUID RHEOLOGY CHARACTERIZATION AND APPARATUS THEREFOR

(75) Inventors: Wei Han, Missouri City, TX (US); John W. Minear, Almont, CO (US); Ronnie G. Morgan, Waurika, OK (US); James R. Birchak, Spring, TX (US)

(73) Assignee: Halliburton Energy Services, Inc., Dallas, TX (US)

( * ) Notice: Subject to any disclaimer, the term of this patent is extended or adjusted under 35 U.S.C. 154(b) by 0 days.

(21) Appl. No.: 09/524,976

(22) Filed: Mar. 14, 2000

(51) Int. Cl.[7] .............................................. G01N 11/00
(52) U.S. Cl. ...................... 73/54.41; 73/53.01; 73/64.53
(58) Field of Search ............................. 73/53.01, 64.53, 73/861.18, 861.25, 54.41

(56) References Cited

U.S. PATENT DOCUMENTS

| | | | | |
|---|---|---|---|---|
| 5,043,706 A | * | 8/1991 | Oliver ........................ | 73/19.03 |
| 6,067,861 A | * | 5/2000 | Shekarriz et al. ......... | 73/861.25 |

OTHER PUBLICATIONS

*Pulsed Ultrasonic Doppler Blood–Flow Sensing*, D. W. Baker, IEEE Transactions on Sonics And Ultrasonics, vol. SU–17, No. 3, Jul. 1970.

* cited by examiner

*Primary Examiner*—Daniel S. Larkin
(74) *Attorney, Agent, or Firm*—William M. Imwalle; Dan Krueger

(57) ABSTRACT

There is disclosed herein a method and apparatus that use ultrasonic signals to measure rheological properties of a fluid flow such as, e.g., the consistency index K, the flow behavior index n', the yield stress $\tau_0$, or other parameters of any given model for shear rate dependent viscosity $\eta$. In one embodiment, the method includes: (a) transmitting an acoustic signal into the fluid flow; (b) receiving acoustic reflections from acoustic reflectors entrained in the fluid flow; (c) determining a Doppler shift of the acoustic reflections in a set of time windows corresponding to a set of desired sampling regions in the fluid flow; and (d) analyzing the Doppler shifts associated with the set of sampling regions to determine one or more rheological properties of the fluid flow. The frequency shift caused by motion of the fluid is proportional to the velocity of the fluid, and this allows the construction of a velocity profile of the fluid flow stream. The velocity profile can be normalized and "matched" to one of a family of velocity profile templates, and the rheological properties identified by the curve that matches best. Alternatively, the shear rate as a function of shear stress can be calculated from the measurements, and these values may be used to find each of the parameters directly. In one embodiment, the apparatus includes a transmitter, a receiver, and an electronic module. The transmitter transmits an acoustic signal into the fluid flow. The receiver receives reflections of the acoustic signal from entrained acoustic reflection sources in the fluid flow. The electronic module is coupled to the transmitter and receiver, and is configured to provide a pulsed high frequency signal to the transmitter and, responsive to the signal from the receiver, to determine a velocity vs. position profile of the fluid flow.

16 Claims, 3 Drawing Sheets

US 6,378,357 B1

METHOD OF FLUID RHEOLOGY CHARACTERIZATION AND APPARATUS THEREFOR

BACKGROUND OF THE INVENTION

1. Field of the Invention

The present invention relates to the measurement of properties of fluids in a flow stream. In particular, the present invention relates to a device and method for measurement of a fluid velocity profile that, in conjunction with a pressure drop measurement, allows for characterization of rheological properties of the fluid.

2. Description of the Related Art

In hydraulic fracture well stimulation operations, fluids such as gelled water fluids and cross-linked gels may be pumped downhole to create and extend fractures and place proppants therein. Fracturing fluid gel primarily contains fresh water (>99.6 % liquid phase), formate brine, diesel, guar (0.2–0.4% w/w liquid), sand (0–33% vol/vol liquid), and crosslinker or breaker polymers (0.1–0.4% vol/vol liquid phase). The preparation of the fracture fluid may involve three stages.

The first stage is the preparation of liquid gel concentrate (LGC). Water and biocide are mixed. Guar powder and diesel are mixed. Two mixtures are pumped separately into a hydration reaction tank. Monitoring of viscosity, density, and flow rates are needed at the inflows to this tank.

The second stage is the hydration reaction of LGC preblend at appropriate pressure and temperature. A viscous fluid (often called clean or base gel) is produced. Monitoring of the viscosity and flow rate is also needed for the base gel stream out of the hydration tank.

The third stage is blending of the base gel with sand and crosslinking agents to form a viscous, sandy gel fluid—the final fracture fluid. This blending may be the most important of the upstream operations. Measurements of viscosity, density, and flow rate of the fracture fluid from this stage are highly preferred. The finished fracture gel is then pumped at pressure (5000–10,000 psi) into distribution pipes and delivered to the well.

In brief, the fracturing fluids generally are non-Newtonian, multiphase fluids containing solid particles, water, and oils. The performance of these fluids is greatly affected by their rheological characteristics. It is greatly desirable to monitor in real time the rheological properties of these fluids over a wide range of shear rates. It would be advantageous for the monitoring apparatus to be non-invasive, and useable on-line, i.e. without disturbing the process flow stream or pumping operations.

As taught by D. W. Baker, "Pulsed Ultrasonic Doppler Blood-Flow Sensing", IEEE Transactions on Sonics and Ultrasonics, Vol. SU-17, No. 3, July 1970, hereby incorporated by reference, ultrasonic signals may be used for non-invasive measurements of fluid velocities. Ultrasonic techniques can provide accurate and reliable measurements. It would be desirable to adapt such techniques to provide a method for fluid rheology characterization.

SUMMARY OF THE INVENTION

The problems outlined above are in large part solved by a method and apparatus using ultrasonic signals to measure rheological properties of a fluid flow such as, e.g., the consistency index K, the flow behavior index n', the yield stress $\tau_0$, or other parameters of any given model for shear rate dependent viscosity $\eta$. In one embodiment, the method includes: (a) transmitting an acoustic signal into the fluid flow; (b) receiving acoustic reflections from acoustic reflectors entrained in the fluid flow; (c) determining a Doppler shift of the acoustic reflections in a set of time windows corresponding to a set of desired sampling regions in the fluid flow; and (d) analyzing the Doppler shifts associated with the set of sampling regions to determine one or more rheological properties of the fluid flow. The frequency shift caused by motion of the fluid is proportional to the velocity of the fluid, and this allows the construction of a velocity profile of the fluid flow stream. The velocity profile can be normalized and "matched" to one of a family of velocity profile templates, and the rheological properties identified by the curve that matches best. Alternatively, the shear rate as a function of shear stress can be calculated from the measurements, and these values may be used to find each of the parameters directly.

In one embodiment, the apparatus includes a transmitter, a receiver, and an electronic module. The transmitter transmits an acoustic signal into the fluid flow. The receiver receives reflections of the acoustic signal from entrained acoustic reflection sources in the fluid flow. The electronic module is coupled to the transmitter and receiver, and is configured to provide a pulsed high frequency signal to the transmitter and, responsive to the signal from the receiver, to determine a velocity vs. position profile of the fluid flow.

BRIEF DESCRIPTION OF THE DRAWINGS

A better understanding of the present invention can be obtained when the following detailed description of the preferred embodiment is considered in conjunction with the following drawings, in which.

Figure 1:
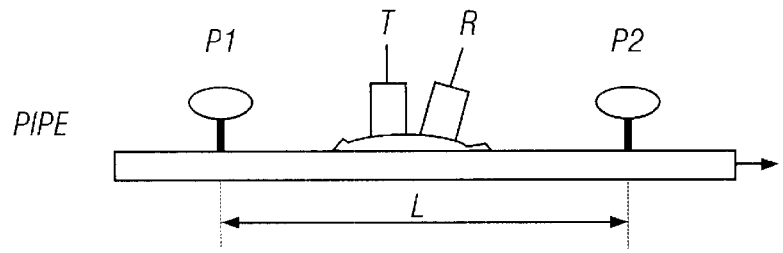
FIG. 1 shows an apparatus for using acoustic signals to determine rheological properties of a fluid flow.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE PREFERRED EMBODIMENT

Turning now to the figures, FIG. 1 shows a cylindrical pipe through which a fluid passes at a relatively steady rate. The fluid flow is preferably in the laminar flow or transitional flow regime, but turbulent flow is also acceptable. Two pressure sensors P1, P2 are shown. They are configured to measure the pressure differential across a pipe region of length L. Length L is preferably at least forty to fifty times the diameter of the pipe. As explained further below, an acoustic transmitter T and acoustic receiver R are acoustically coupled to the fluid passing through the pipe and are used to determine the shear rate profile of the fluid flow in the pipe region between the pressure sensors. Suitable pressure sensors are well known to those of skill in the art, and will not be discussed further.

It is not necessary for the transmitter or receiver to be directly mounted on the pipe. Indeed, there may be advantages to establishing an acoustic coupling via a liquid medium in terms of reduced reverberation in the pipe walls.

A preferred embodiment of the acoustic transducer electronics is now described with reference to FIG. 2. In the preferred embodiment, a pulsed Doppler backscatter technique is used. This technique relies on determination of the frequency shift or time domain shift of backscattered signals reflecting off of particles or bubbles in a flowing fluid. This shift is preferably obtained as a function of spatial range.

From these measurements, a velocity profile of the fluid flow can be calculated. From a single velocity profile at a measured pressure gradient, fluid rheological properties can be obtained over shear rates ranging from zero at the center of the tube to the maximum shear rate at the tube wall. The rheological parameters, such as, e.g., shear rate-dependent viscosity η, consistency index K', flow-behavior index n', yield stress $\tau_0$, etc., that are used in a chosen rheological model, can be determined from the measurement of the shear stress—shear rate relationship. Advantageously, ultrasonic techniques can provide noninvasive, accurate, and reliable measurements.

Figure 2:
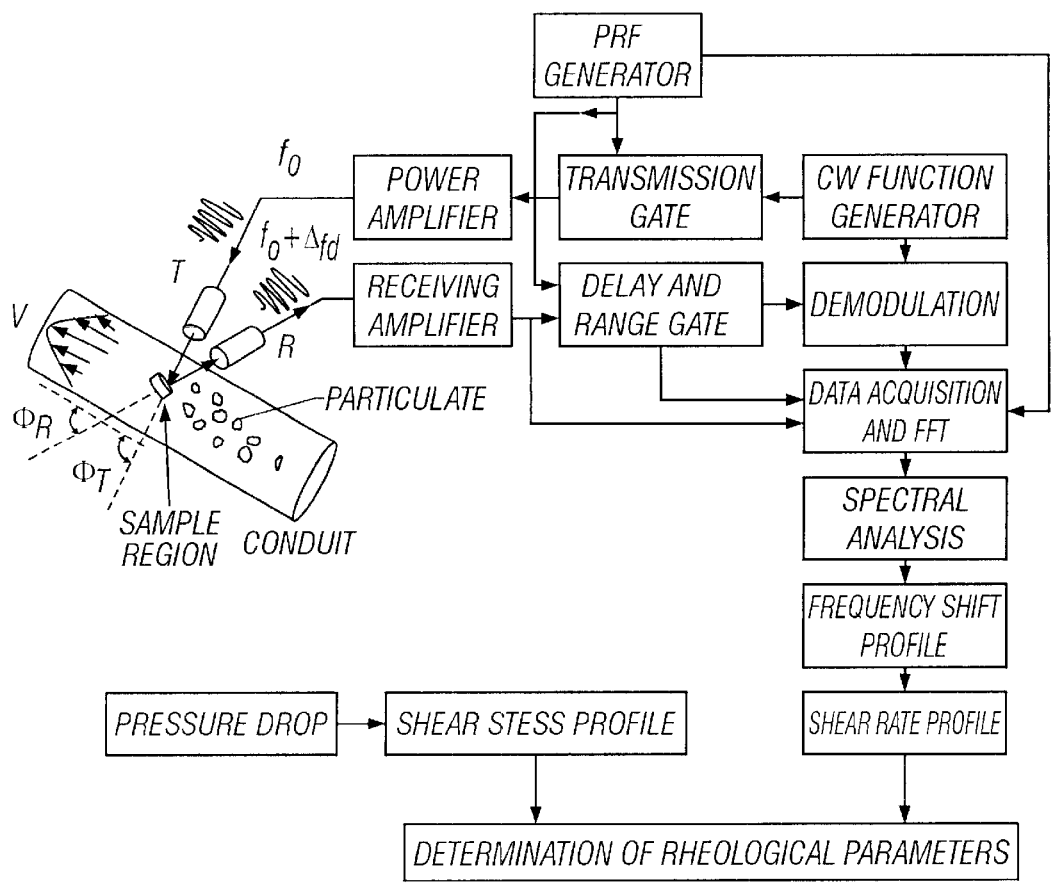
FIG. 2 shows a functional block diagram of the apparatus.

In the embodiment of FIG. 2, a pulsed repetitive frequency (PRF) signal generator produces a sequence of pulses. A continuous wave signal generator preferably produces a sinusoidal signal at a programmable frequency. A transmission gate receives the sinusoidal signal and the PRF signal and "gates" the sinusoidal signal using the PRF signal. In one embodiment, the transmission gate suppresses the sinusoidal signal when the PRF signal is de-asserted, and passes the sinusoidal signal when the PRF signal is asserted. In another embodiment, the transmission gate is a mixer that amplitude modulates the sinusoidal signal with the PRF signal. This second embodiment allows for sophisticated shaping of the PRF signal if it is desired to control the frequency content of the output signal. The output signal is amplified by a power amplifier and converted to an acoustic signal by acoustic transmitter T.

The sinusoidal signal frequency is preferably somewhere in the megahertz range (0.5–500 MHz). The transmission gate preferably provides a pulse width of at least five sinusoidal signal cycles with the pulse repetition frequency rate greater than twice the maximum expected Doppler frequency shift. The "off" period between pulses is preferably long enough to permit any reverberation and echoes from one pulse to die out before the subsequent pulse is transmitted. In one configuration, a 10 MHz carrier is used to create a 100 KHz pulse sequence with a pulse width of one microsecond.

The acoustic transmitter preferably transmits a collimated or focused beam of acoustic energy into the fluid flow stream. There, some of the acoustic energy reflects off of impedance mismatches, such as those caused by bubbles, particulates, and emulsified droplets of different phases, in the path of the beam. Motion of the bubbles, particulates, etc. causes the reflected acoustic energy to have a different frequency than the transmitted acoustic energy. The shift in the frequency is proportional to the velocity of the reflection sources.

Figure 3:
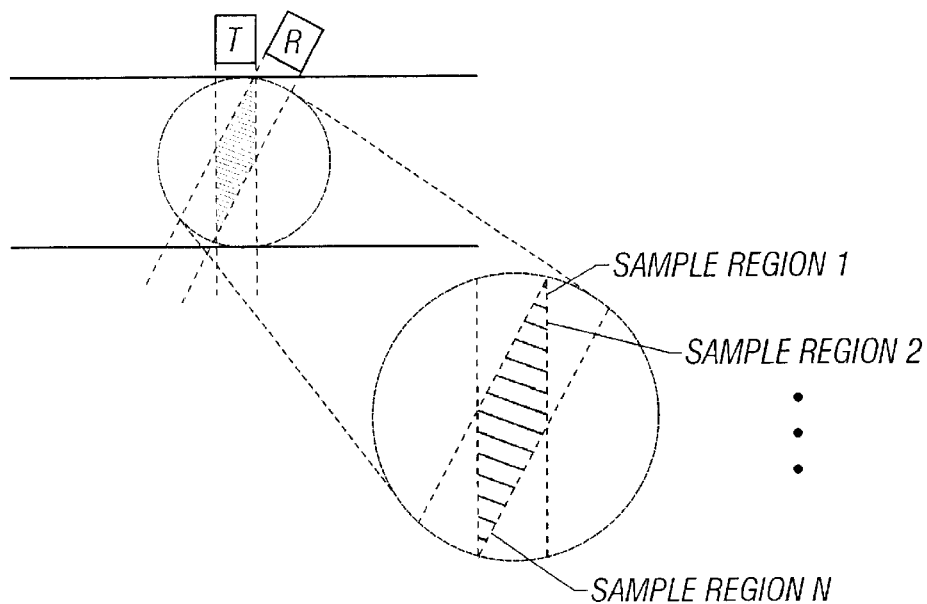
FIG. 3 shows a schematic view of the insonification field and one method for dividing the insonification field into multiple sample regions.

Referring momentarily to FIG. 3, the acoustic receiver detects acoustic energy traveling in the direction of the receiver from a beam-shaped region in from of the receiver. The transmit and receive beams overlap, and the region of overlap preferably extends at least from near one wall of the pipe to the center of the pipe. The region of overlap in FIG. 3 extends from the near wall of the pipe to the far wall. A timing circuit discussed further below will be used to divide the overlap region into a series of sample regions. The sample regions may be adjacent or spaced-apart, but in the preferred embodiment, they overlap slightly. The sample region may be determined by "time-gating" the received signal, so that only the signal that corresponds to a selected range of acoustic travel times is processed. In the preferred embodiment, only a single sample region is processed at a time, although in an alternative embodiment, multiple sample regions are processed in parallel.

Dividing the overlap region in this manner makes it possible to identify fluid velocities in sample regions at various radial distances from the center of the pipe. A velocity profile (i.e. the velocity as a function of radial position) of the fluid flow in the pipe can be obtained by measuring the frequency shift caused by reflections in each sample region.

Returning to FIG. 2, the acoustic energy reflected by acoustic impedance mismatches in the overlap region is received by the acoustic receiver and converted into an electric signal that is buffered and amplified by a receiving amplifier. A delay and range gate receives the PRF signal and the receive signal. The delay and range gate includes a timing circuit that is configured to produce a one-shot pulse of predetermined width at a programmable delay after each rising edge of the PRF signal. This delayed pulse signal is used to gate the receive signal in a manner similar to the transmission gate. The gated receive signal is provided to a demodulator.

The demodulator multiplies the sinusoidal signal of the continuous wave function generator with the gated receive signal to provide a product signal. The demodulator low-pass filters the product signal (above half of the PRF frequency) to provide a frequency shift sample signal. The demodulator also high-pass filters the mixed signal to remove any low-frequency signal (below 100 Hz) caused by the reverberation of the pipe. Because the gated receive signal is a sequence of pulses, the demodulated signal is also a sequence of pulses that contains the Doppler frequency shift to be measured. During the gated receive signal pulses, the frequency shift sample signal is proportional to the cosine of the phase difference between the sinusoidal signal and the gated receive signal. The value of the frequency shift sample signal pulses will oscillate at a frequency that is equal to the frequency difference between the sinusoidal signal and the gated receive signal.

A data acquisition block receives the delayed pulse signal and uses it as a clock signal to digitally sample the frequency shift signal pulses. A fast Fourier Transform (FFT) is applied to the digital frequency shift signal, and a spectral analysis block determines the frequency of the frequency shift signal. As each sample region contains components of different velocities, a frequency shift spectrum is thus obtained. Thus the mean frequency shift of the spectrum is proportional to the mean velocity of the fluid in the sample region, so the velocity may be determined by multiplying the frequency from the spectral analysis block by a calibration constant.

A controller (not shown) adjusts the programmable delay of the delay and range gate to obtain the frequency shifts in various sample regions. It is noted that the transmission gate and delay and range gate may also be bypassed if it is desired to obtain an average velocity measurement for the fluid stream as a whole.

A frequency profile block gathers the frequency shifts to build a frequency shift profile, from which a shear rate profile can be determined. The measured pressure drop is combined with the known geometry of the system to determine the shear stress profile. The controller may combine the shear stress profile with the shear rate profile to determine the desired rheological parameters as described further below.

In one embodiment, the radial position of the various sample regions may be predetermined. However, in the preferred embodiment, the controller is able to measure the average speed of sound in the fluid and use that to calculate the radial position of the various sample regions. The data acquisition block may be configured to measure the time difference between the echo off the near wall of the pipe and the echo off the far wall of the pipe. This time difference, in conjunction with geometrical information and calibration constants that can be predetermined, allows the controller to calculate the average speed of sound in the fluid.

To summarize, the frequency shift is proportional to the velocity of the fluid at a specific depth in the fluid. A short tone-burst sine wave of several cycles is transmitted by a transducer into the flowing media. A receiving transducer detects a series of reflected signals. A properly gated time window, corresponding to flow at a specific depth, is opened after a predetermined time delay. The signals within each time window can be digitized and analyzed using known mathematical algorithms to obtain a frequency spectrum. The mean frequency shift, proportional to the mean flow velocity in the gated window, is determined from the spectrum. Thus, by varying the delay time, a series of mean frequency shifts $f_d$ measured from each frequency spectrum of the gated window, can be determined over the range of delay times T.

Figure 4:
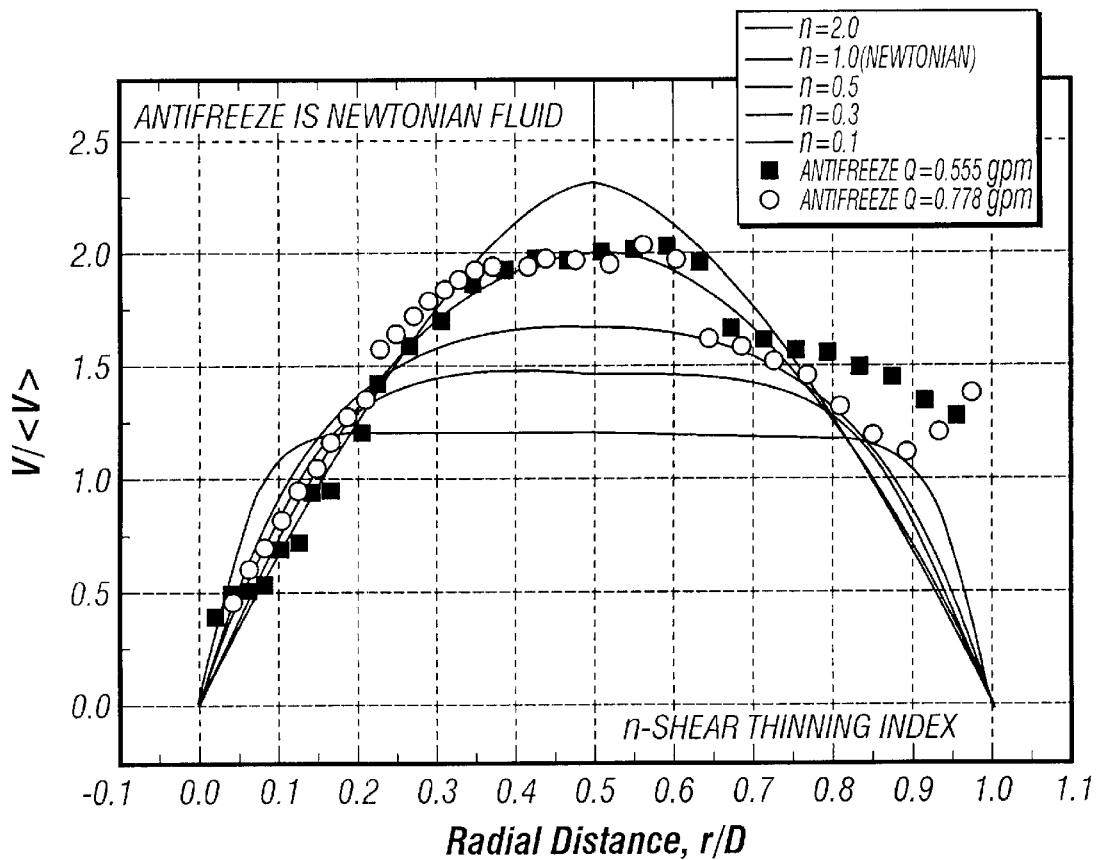
FIG. 4 shows a comparison of model velocity profiles with experimental velocity profiles.

For fully developed, steady laminar flow (i.e., Reynolds number Re<2100, Re=2RVρ/η, where R is the tube radius, V is the average velocity, ρ is the fluid density, and η is the apparent viscosity), fluid rheological parameters may be determined by comparing the measured velocity profile $V/V_{avg}$ vs. r/R to model profiles to determine which model profile fits best. The average velocity $V_{avg}$, can be obtained from volume flow rate ($V_{avg}=Q/\pi R^2$) or calculated from integration of the measured velocity profile over r/R, or obtained from acoustic measurement. A least-mean square error curve fitting technique may be used. FIG. 4 shows the velocity profiles for five "power law" fluids having different consistency indices n'. Experiments on a suspension of 5 wt % Deae-Sepharcel particle in antifreeze liquid in a ⅜ inch inner diameter plastic tube using two different flow rates showed that, as expected, antifreeze behaves as a Newtonian fluid (n'=1). It is noted that, due to the symmetry of the fluid flow pattern, it may be sufficient to measure flow velocities on only one side of the centerline.

Figure 6:
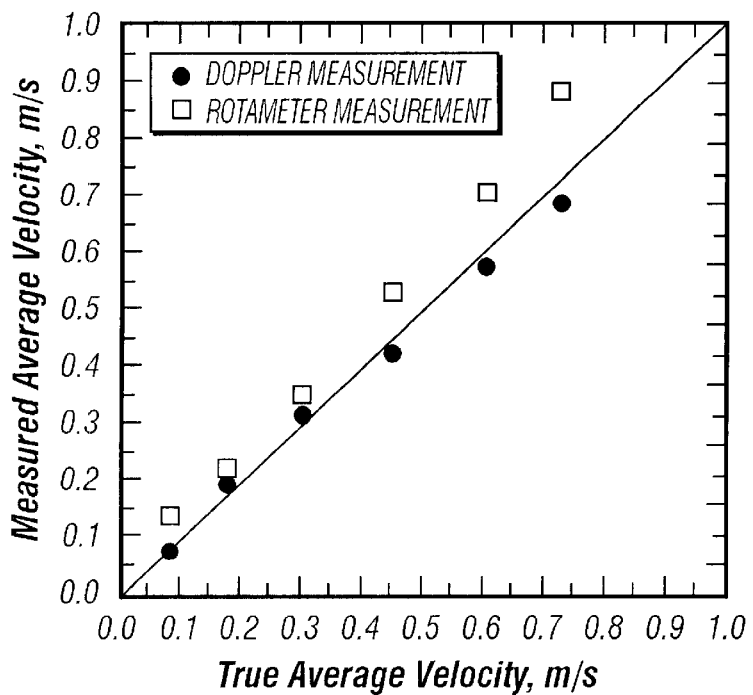
FIG. 6 shows a comparison of average Doppler velocity measurement with actual fluid velocity.

As an aside, in the same experimental system, FIG. 6 shows the average fluid flow velocities measured by continuous ultrasonic Doppler shift method and by a rotameter, as compared with the actual average fluid flow velocity (x-axis). A good agreement is observed for the Doppler measurement.

Alternatively, or additionally, the rheological parameters of the fluid may be calculated. For tube flow, the shear rate profile is the derivative of velocity as a function of radial position, or dV/dr. Given the relationship of $f_d$ as a function of delay time T, the shear rate profile can be found by taking the derivative:

$$dV/dr = A\, df_d/dT,$$

where, $A=2/[f_0(\cos \phi_T + \cos \phi_R)]$, is a constant related to the transmitting frequency $f_0$ and the angles of the transmitter and receiver relative to the flow direction, $\phi_T$, $\phi_R$.

Therefore, shear rate profile over the tube radial distance dV/dr can be determined from the Doppler frequency shift profile over the delay time range $df_d/dT$. Speed of sound of the flowing fluid is not required in the determination of shear rate profile, which is also affected by the frequency and the angles of the transducers relative to the flow direction.

Given the pressure drop of ΔP between two points along the tube length, L, measured by the previously mentioned pressure sensors, the shear stress at radius r is calculated to be:

$$\tau_r = [\Delta P r/(2L)].$$

In laminar flow, the distribution of shear stress in the fluid is linear from zero at the centerline to the maximum at the tube wall. The apparent viscosity corresponding to the shear rate at depth r, is given by:

$$\eta = \tau_r/[dV/dr]_r.$$

From the measured relationship between apparent viscosity and shear rate, the non-Newtonian fluid model parameters, such as K' and n' for "power-law fluids" (e.g. fracturing gels), can be determined.

Power-law fluids have a shear stress relationship with the shear stress $$\tau = K(\dot{\gamma})^{n'}$$

and apparent viscosity $$\eta = K(\dot{\gamma})^{n'-1}.$$

Figure 5:
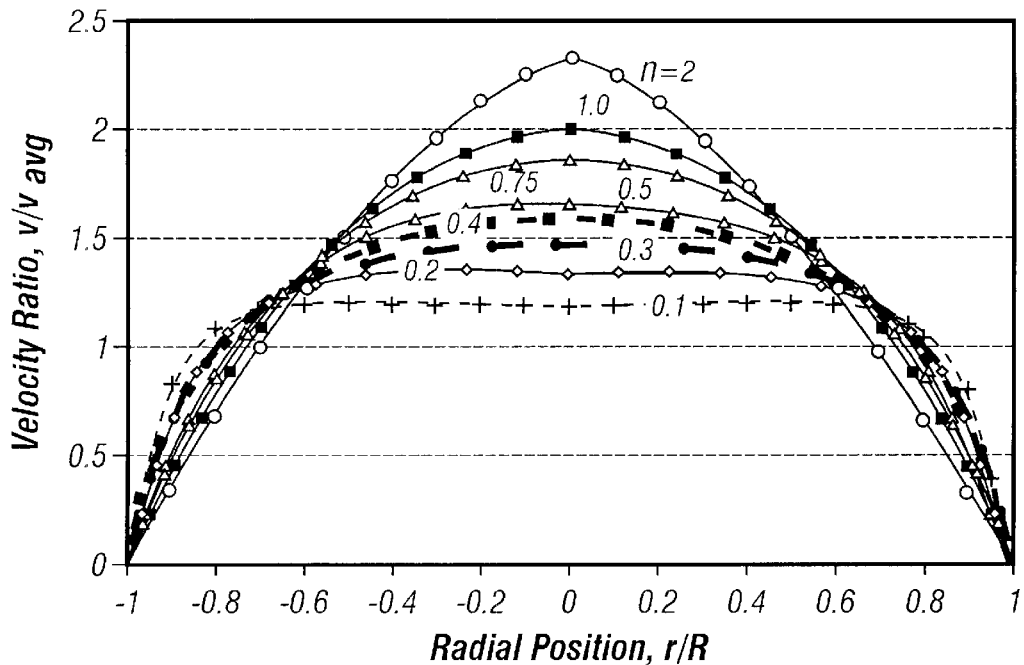
FIG. 5 shows a family of velocity profiles for power law fluids.

K and n' are the consistency index and the flow behavior index respectively, two unique fluid parameters to be characterized. For Newtonian fluids, K=μ (fluid viscosity), and n'=1.0. FIG. 5 shows some typical velocity profiles for power-law fluids in tube. Linear gel fluids are usually pseudoplastic with n'=0.4 to 0.5. Typical features for the non-Newtonian fluids (n'<1) are that the normalized velocity is almost unchanged in the center region of the pipe (0<r/R<0.5), and that a velocity gradient exists only in the outer region (0.6<r/R<1.0). It is noted that the power law model is only one of several possible models, and that other models may also be used (e.g. the generalized non-Newtonian Model).

With volumetric rate Q through a pipe of R radius, shear stress at the pipe wall is given $$\tau_w = \frac{\Delta P R}{2L}.$$

Here ΔP is pressure drop over length L and can be measured by pressure sensors. Parameter n' can be calculated by $$n' = \frac{d\ln(\tau_w)}{d\ln\left(\frac{4Q}{\pi R^3}\right)},$$

obtained from appropriate range of flow rate and corresponding pressure gradient. It is noted that non-Newtonian fluids have almost constant velocity gradient dV/dr over the boundary layer near the wall, so that it should be possible to make only a few measurements of velocity within the boundary layer to estimate the parameters with ascertained accuracy. Since the needed penetration depth is thin, a high frequency (e.g., 15 MHz) transmission can be applied and signal resolution can be thereby enhanced.

From the model, the shear rate at the pipe wall is expected to be $$\dot{\gamma}_w = \frac{3n'+1}{4n'}\frac{4Q}{\pi R^3}.$$

Thus, one n' has been found, the factor $$K = \tau_w/(\dot{\gamma}_w)^{n'}$$

can be obtained. Therefore, both parameters K and n' of the apparent viscosity model $$\eta = K(\dot{\gamma})^{n'-1}$$

can be found from the determination of shear rate $$\dot{\gamma} = \frac{dV}{dr}$$

from the measured velocity profile.

For transition or turbulent flow regimes (Re>2100), a velocity gradient or profile still exists in a thin boundary layer near the pipe wall that can be measured by the disclosed pulsed Doppler technique. Shear stress profile still exists in the thin layer as given by $\tau_r = [\Delta PR/(2L)] (r/R)]$, where r is the turbulent layer boundary thickness (Transport Phenomena by Bird, Stewart and Lightfoot, pp 162, Eq. 5.3–7, incorporated herein by reference).

In an alternative embodiment, the relationship between apparent viscosity and multiple shear rates may be determined from measurements within the turbulent boundary layer. This should also provide enough information to calculate rheological parameters. High frequency signals and/or focusing of the acoustic beam may be used for accurate measurements in the fluid flow regime close to the wall, permitting the Doppler frequency shifts due to the turbulent velocity profile in the boundary region close to the wall and in the main stream flow to be measured separately. This allows for the determination of the shear rate associated with the turbulent flow and the non-Newtonian rheological properties.

It is noted that as an alternative to the pulsed Doppler frequency shift measurement method described above, a time domain shift method may be used. As an example, a transmitter emits a sequence of high frequency acoustic pulses. The signal received by an acoustic receiver in response to each pulse is an echo train. Using cross-correlation techniques to compare a selected time window of one echo train to a subsequent echo train will reveal a time delay caused by motion of the reflection sources. Measuring the time delay as a function of the radial position of the reflection sources allows for the calculation of a velocity profile, which is then used as described above.

Continuous ultrasonic Doppler measurement can be also used to obtain the average flow velocity of across the tube. For this measurement, continuous sine waves, rather than the tone-burst sine waves in the pulsed measurement, are transmitted. The shear stress-shear rate relationship may be obtained by measuring a series of averaged velocities made at different pressure gradients. Also the measurement ranges of shear rate and shear stress can be extended by varying the flow rate, the tube diameter, or the pressure gradient.

The disclosed apparatus can, in principle, not only provide a powerful means for flow profile and rheology measurement, but also serve as a potential tool for characterization of multiple phase fluids and for process control and monitoring. Potential applications may include among other things: monitoring of concentration and viscosity, monitoring of hydration reaction and cross-linking mixing, and fracturing gel pumping operation, smart well permanent sensors, cutting transport monitoring, etc.

Numerous other variations and modifications will become apparent to those skilled in the art once the above disclosure is fully appreciated. For example, additional transmitters or receivers may be provided to increase accuracy and sensitivity. Two or more transmitter-receiver pairs may be used to assess different regions inside the tube. One pair may have a high frequency response, with the angle and position chosen so that the field of the insonification overlaps the boundary of the inner wall of the pipe and the fluid. Another pair may have a lower frequency resonance and be positioned so that the overlapping volume covers a specific region, e.g. the center of the tube. Other tubing cross-sections may also be employed. It is intended that the following claims be interpreted to embrace all such variations and modifications.

What is claimed is:

1. A method for measuring rheological properties of a fluid flow having entrained acoustic reflectors, wherein the method comprises:

transmitting an acoustic signal into the fluid flow;

receiving acoustic reflections from the entrained acoustic reflectors;

determining a Doppler shift of reflections in a plurality of time windows corresponding to a plurality of sampling regions in the fluid flow; and processing the Doppler shifts associated with sampling, regions to determine one or more rheological properties of the fluid flow, wherein the processing includes:

matching a velocity vs. position relationship curve to the Doppler shifts associated with their sampling regions; and identifying one or more theological properties of the fluid flow from the relationship curve that matches best.

2. The method of claim 1, wherein the one or more rheological properties includes the consistency index K and the flow behavior index n'.

3. The method of claim 1, wherein the one or mote rheological properties includes the yield stress $\tau_0$.

4. The method of claim 1, wherein the one or more rheological properties are the parameters of a model for shear rate-dependent viscosity $\eta$.

5. A method for measuring rheological properties of a fluid flow having entrained acoustic reflectors, wherein the method comprises:

transmitting an acoustic signal into the fluid flow;

receiving acoustic reflections from the entrained acoustic reflectors;

determining a Doppler shift of reflections in a plurality of time windows corresponding to a plurality of sampling regions in the fluid flow;

processing the Doppler shifts associated with sampling regions to determine one or more rheological properties of the fluid flow; and measuring, a pressure drop experienced by the fluid flow.

6. The method of claim 5, wherein said processing includes:

calculating a shear stress at each of a plurality of positions in the fluid flow.

7. The method of claim 6, wherein said processing further includes:

from the Doppler shifts, identifying a shear rate at each of said plurality of positions in the fluid flow; and calculating an apparent viscosity associated with each of said identified shear rates.

8. The method of claim 7, wherein said processing further includes:

operating on the calculated apparent viscosities to find one or more parameters of a model for the apparent viscosity.

9. The method of claim 8, wherein said model is a power-law fluid model.

10. An apparatus for determining one or more properties of a fluid flow having entrained acoustic reflection sources, wherein the apparatus comprises:

a transmitter configurable to transmit an acoustic signal into the fluid flow;

a receiver configurable to receive reflections of the acoustic signal from the entrained acoustic reflection sources; and an electronic module coupled to the transmitter and receiver, and configured to provide a pulsed high frequency signal to the transmitter and to determine a velocity vs. position profile of the fluid flow, wherein the electronic nodule includes:

a pulse signal generator configured to generate a pulse signal;

a sinusoidal signal generator configured to generate a sinusoidal signal; and a transmission gate coupled to the pulse signal generator and the sinusoidal signal generator and configured to combine the pulse signal with the sinusoidal signal to produce the pulsed high frequency signal.

11. The apparatus of claim 10, wherein the electronic module further includes:

a range gate coupled to the receiver and to the pulse signal generator, and configured to pass a portion of the receive signal in an adjustable time window relative to the pulse signal, thereby providing a gated receive signal;

a demodulator coupled to the sinusoidal signal generator and to the range gate, and configured to combine the sinusoidal signal with the gated receive signal to produce a frequency shift sample signal; and a data acquisition module coupled to the demodulator and configured to perform a transform operation on the frequency shift sample signal to determine a frequency shift associated with a region of the fluid flow corresponding to the current time window.

12. The apparatus of claim 11, wherein the electronic module is configured to adjust the time window to determine the frequency shifts associated with a plurality of regions in the fluid flow, and is further configured to determine one or more apparent viscosity model parameters of the fluid flow from the frequency shifts.

13. An apparatus for determining one or more properties of a fluid flow having entrained acoustic reflection sources, wherein the apparatus comprises:

a transmitter configurable to transmit an acoustic signal into the fluid flow;

a receiver configurable to receive reflections of the acoustic signal from the entrained acoustic reflection sources;

an electronic module coupled to the transmitter and receiver, and configured to provide a pulsed high frequency signal to the transmitter and to determine a velocity vs. position profile of the fluid flow; and one or more pressure sensors configured to determine a pressure drop experienced by the fluid flow, wherein the electronic module is coupled to the one or more pressure sensors and configured to calculate a shear stress on the fluid flow.

14. An apparatus for determining one or more properties of a fluid flow having entrained acoustic reflection sources, wherein the apparatus comprises:

a transmitter configurable to transmit an acoustic signal into the fluid flow;

a receiver configurable to receive reflections of the acoustic signal from the entrained acoustic reflection sources; and an electronic module coupled to the transmitter and receivers, and configured to provide a pulsed high frequency signal to the transmitter and to determine a velocity vs. position profile of the fluid flow, wherein the fluid flow is turbulent.

15. An apparatus for determining one or more properties of a fluid flow having entrained acoustic reflection sources, wherein the apparatus comprises:

a transmitter configurable to transmit an acoustic signal into the fluid flow;

a receiver configurable to receive reflections of the acoustic signal from the entrained acoustic reflection sources; and an electronic module coupled to the transmitter and receiver, and configured to provide a pulsed high frequency signal lo the transmitter and to determine a velocity vs. position profile of the fluid flow, wherein the fluid flow has a Reynolds number greater than 2300.

16. An apparatus for determining one or more properties of a fluid flow having entrained acoustic reflection sources, wherein the apparatus comprises:

a transmitter configurable to transmit an acoustic signal into the fluid flow;

a receiver configurable to receive reflections of the acoustic signal from the entrained acoustic reflection sources; and an electronic module coupled to the transmitter and receiver, and configured to provide a pulsed high frequency signal to the transmitter and to determine a velocity vs. position profile of the fluid flow, wherein the fluid flow is tubular shear flow.

\* \* \* \* \*